US006337483B1

(12) United States Patent
Matschke

(10) Patent No.: US 6,337,483 B1
(45) Date of Patent: Jan. 8, 2002

(54) APPARATUS AND METHOD FOR SIMULTANEOUSLY GERMICIDALLY CLEANSING BOTH AIR AND WATER

(75) Inventor: Arthur L. Matschke, Bridgewater, CT (US)

(73) Assignee: MolecuCare, Inc., New Milford, CT (US)

(*) Notice: Subject to any disclaimer, the term of this patent is extended or adjusted under 35 U.S.C. 154(b) by 0 days.

(21) Appl. No.: 09/654,725

(22) Filed: Sep. 5, 2000

Related U.S. Application Data

(63) Continuation-in-part of application No. 09/499,597, filed on Feb. 7, 2000, now Pat. No. 6,228,327, which is a continuation-in-part of application No. 09/112,500, filed on Jul. 9, 1998, now Pat. No. 6,022,511.

(51) Int. Cl.[7] .................................................. A61L 9/20
(52) U.S. Cl. ................... 250/432 R; 250/435; 250/436; 422/24; 422/121
(58) Field of Search .................................. 250/436, 435, 250/432 R, 455.11; 422/24, 121

(56) References Cited

U.S. PATENT DOCUMENTS 2,183,498 A * 12/1939 Anderson ............... 250/432 R
5,612,001 A *  3/1997 Matschke .............. 250/455.11

* cited by examiner

Primary Examiner—Jack Berman
(74) Attorney, Agent, or Firm—Bazerman & Drangel, PC

(57) ABSTRACT

A germicidal UV chamber for use on air passing through a duct system, such as a central air system which replace one or more sections of the duct and, in essence, becomes part of the duct work. Each chamber is in the form of one or more ellipsoid sections which focus the energy uniformly throughout the chamber. The inlet and exit passages from the chamber are a grill formed from truncated elliptical concentric rings. Also positioned in the chamber is an ultraviolet transparent conduit through which a liquid such as water passes and is also germicidally cleansed. The conduit may very in diameter to retain UV energy in the conduit.

20 Claims, 8 Drawing Sheets

US 6,337,483 B1

APPARATUS AND METHOD FOR SIMULTANEOUSLY GERMICIDALLY CLEANSING BOTH AIR AND WATER

This application is a continuation-in-part of U.S. patent application Ser. No. 09/499,597, filed Feb. 7, 2000, now U.S. Pat. No. 6,228,327, which in turn is a continuation-in-part of U.S. Pat. No. 6,022,511, issued Feb. 8, 2000.

BACKGROUND OF THE INVENTION

Airborne bacteria or other microorganisms permeate the air we breath and the water we drink. Some of these microorganisms with which we share our environment cause disease. Medical environments, such as hospitals, have a high degree of pathogens in the air and water and highly susceptible, weakened patients. The existence of biological weapons of mass destruction require protection of command centers, barracks, ships, and other closed environments against biological agents. Today's modem sealed high-rise structures with central air conditioning and heating, through duct systems, need protection from the spread of disease among its occupants and from colonies of microorganisms which may live in the duct and water system. Today, biologic protection is necessary on the battlefield and in the workplace, the hospital and the home.

Much effort has gone into trying to destroy atmospheric pathogens with only limited success. It has long been recognized that pathogens can be destroyed in the air if they are irradiated with ultraviolet (UV) light at a wavelength of 253.7 nanometers (Germicidal Wavelength). In order for the UV light to kill microorganisms, the UV rays must directly strike the microorganisms for a sufficient time. Because of the absolute necessity for antiseptic surroundings, UV lamps of the required Germicidal Wavelength are often used in operating rooms, wards, and nurseries of hospitals.

The exposure to UV light necessary to kill microorganisms is a product of time and intensity. However, due to the dangers to humans of irradiation from wide-spread use of UV lamps, exposure to UV light has been limited by government regulations. The current occupant exposure limit (ACGIH, NIOSH standard) for 254 m ultraviolet germicidal wavelength ceiling fixtures is 6000 $\mu$watts seconds/cm$^2$ in one eight hour day. Thus, the maximum allowed intensity per second is 0.2 $\mu$W/cm$^2$. At this intensity, eight hours at the allowed exposure level is required to gain a 90% kill of *Mycobacterium tuberculosis* (90% kill-value= 6200 $\mu$watts/cm$^2$) at head height. For 100% kill using the same standard, the value is 10,000 $\mu$watts/cm$^2$, requiring 13.89 hours of exposure. The required low intensity, and resulting long exposure times, permit migration of microorganisms out of range of the UV lamp and result in accumulation of microorganisms which survive the UV lamp in the room. Increasing air circulation does not increase exposure of microorganisms. It only moves organisms past the UV lamp without sufficient exposure.

To overcome these problems there have been various attempts to circulate air passed UV sources in enclosures which acts to shield the UV irradiation from the room's occupant. Usually, such systems are free-standing, or wall or ceiling mounted devices which circulate the air in a single room through the enclosure and, accordingly, whose protection is confined to that room. See, for example, U.S. Pat. No. 5,330,722 to Pick, which discloses a germicidal air purifier which draws air through a chamber in which there is mounted an ultraviolet source which acts to kill microorganisms caught in the filter structure. Similarly, U.S. Pat. No. 5,612,001 to Arthur L. Matschke, discloses a germicidal air cleansing enclosure having an internal ellipsoid chamber which contains UV lamps along the major axis of the ellipsoid. The unit is free-standing and treats air in a single room.

While a system such as that disclosed in U.S. Pat. No. 5,612,001 to Arthur L. Matschke, may be highly effective to cleans the contents of a single room, normal air conditioning and heating ducts would continue to allow circulation of untreated air into and out of a room. This allows untreated air containing pathogens from another room, or in the duct system, to enter the room and come into contact with humans before being treated and allow a certain amount of pathogens in a room to enter the duct system prior to being treated by the free-standing unit.

Various attempts have been made to place ultraviolet light sources in duct systems to germicidally cleans fluids such as air as they pass through the duct system. See, for example, U.S. Pat. No. 5,635,133 to Glazman, U.S. Pat. No. 5,200,156 to Wedekamp and U.S. Pat. No. 5,107,687 to Candelares. Each of these patents disclose an ultraviolet irradiation source in a duct to cleanse a fluid traveling through a duct of uniform diameter. The UV source is at right angles to the duct walls and UV energy is directed at least in part along the path of fluid flow. Thus, the level of ultraviolet energy varies along the flow path. As a result, the air circulated past the UV lamps in the prior art receive an uneven distribution of ultraviolet energy and a rapid diminution of energy levels outside the immediate area of the UV source. The grandparent of the present patent application, now U.S. Pat. No. 6,022,511, to Matschke, discloses an ellipsoidal, ultraviolet reflective chamber mounted in a duct system which exposes the air passing through the chamber to sufficient UV energy to germicidally cleanse all of such air. However, it does not provide the means for treating water in the same closed environment.

Bacteria or other microorganisms not only permeate the air we breath but also the water we drink. Much effort has gone into trying to limit or destroy water-borne pathogens. It has long been recognized that pathogens can also be destroyed in water if they are irradiated with ultraviolet (UV) light of a wavelength of 253.7 nanometers. In order for the UV light to kill microorganisms, and particularly pathogens, the rays must directly strike them. U.S. Pat. No. 5,874,741 to Matschke discloses an ellipsoid, ultraviolet reflective chamber to expose water passing through the chamber to sufficient UV energy to germicidally cleanse all of such water.

SUMMARY OF THE PRESENT INVENTION

It is an object of the present invention to provide an ultraviolet chamber for simultaneous processing of air and water which combines both optics and air and water flow techniques to kill microorganisms present in the air and water.

It is a further object of the present invention to cause all air and water flowing throughout the present invention to be exposed at a uniform constant rate of high levels of ultraviolet radiation.

It is a further object of the present invention to do so with no ultraviolet exposure to humans.

The present invention is a germicidal chamber which uniformly irradiates all of the air passing through a duct system in which it is mounted, such as a central air system. The chamber replaces one or more sections of the duct and, in essence, becomes part of the duct work. The chamber has running along the chamber's longitudinal axis an ultraviolet transparent pipe through which water or other fluid may pass. The ultraviolet transparent pipe is attached at or near both ends of the ultraviolet chamber to conventional pipes which passes through the wall either of the duct or the chamber and form part of the fluid circulatory system, such as a buildings water supply. The ultraviolet transparent conduit or pipe may be tapered in order to reflect ultraviolet energy back into the water, thereby increasing the intensity of ultraviolet treatment of the water as it passes through the chamber.

Each chamber is in the form of one or more ellipsoid sections which focus the energy uniformly throughout the chamber. A sphere is a form of ellipsoid and can be used in carrying forward the present operation. The chamber is connected to the duct so that all air drawn into the duct system must pass through the chamber. To accomplish this, each chamber is integral with the duct forcing all of the air in the duct on the upstream side to pass through the chamber. In order to eliminate back pressure which might arise from any impediment to the flow of air through the chamber while allowing reflection of all of the ultraviolet radiation back into the chamber, a grille formed from concentrical ellipsoid sections is positioned at each end of the chamber so that substantially all of the ultraviolet radiation is reflected back into the chamber while allowing relatively unimpeded flow of the air through the chamber.

It has also been found that the dispersion of ultraviolet light in the chamber can be improved by the use of a helically wound ultraviolet light source positioned around the major axis of the chamber. The helically wound ultraviolet light source may be positioned around the ultraviolet transmission pipe carrying the fluid to be treated. The geometric center point of the chamber is the point within the chamber from which light will travel the greatest distance before a first reflection, incident with the wall and, thus, the first absorption of energy. Thus, the efficiency of the light source decreases as the point of origin of the light source moves away from the center of the axis of the ellipsoid chamber as a product of the energy absorption and the subsequent infinite reflections through the enclosure. Accordingly, the helical light source is more closely wound towards the center of the chamber to increase the efficiency in the even distribution of ultraviolet light throughout the chamber.

A combined air/water chamber of this type is not only highly useful in structures such as hospitals, office towers, homes, anti-germ warfare structures and the like, but is useful in any closed environment where a large number of people are situated in relative proximity such as on airplanes or buses. In such environments, the present invention not only protects against infection but reduce the amount of water, and thus dead weight, to be carried.

DESCRIPTION OF THE PREFERRED EMBODIMENT

Figure 1:
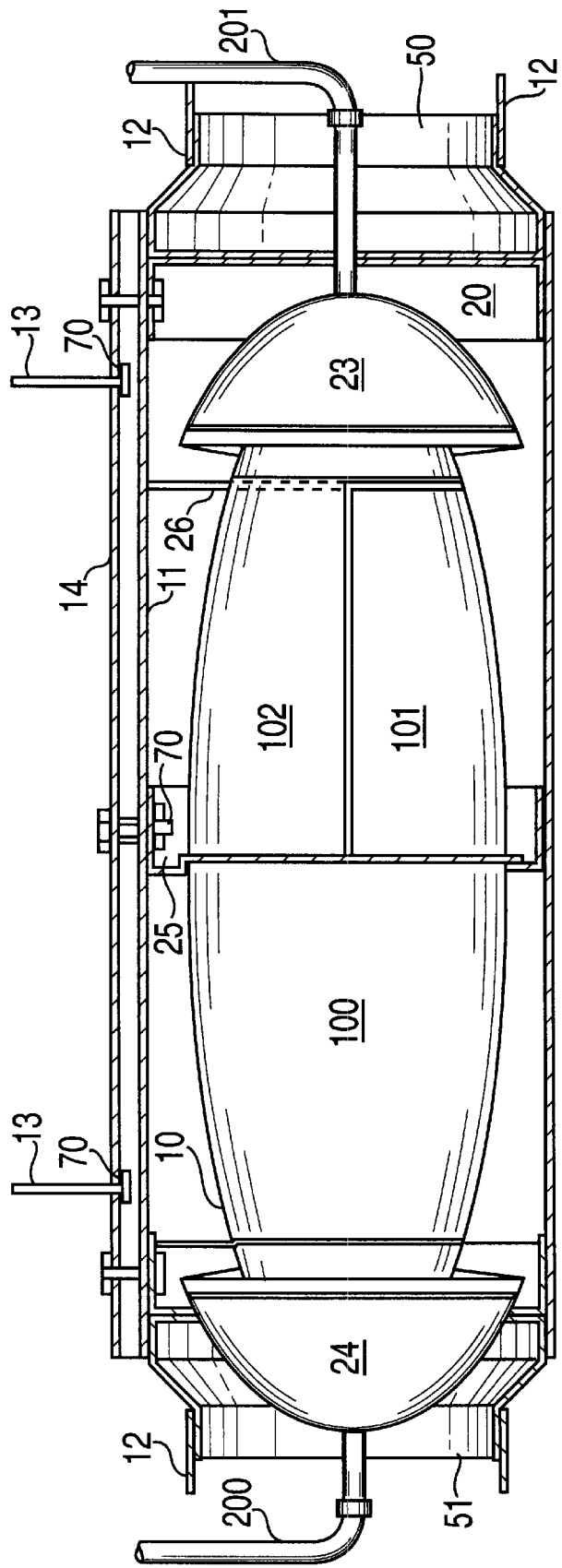
FIG. 1 is a partial cut-away front view of a chamber, in accordance the present invention, with the shell wall partially removed.

In the present invention, the duct work of a central air system is modified to replace a portion of the duct with an ellipsoidal UV chamber 10 which becomes part of the central air duct system. Air is normally circulated through the central air system including through the chamber 10 by the HVAC fan.

The germicidal cleansing chamber 10 is mounted within a shell 11 connected to an air duct 12. The shell 11 can be used to insulate the chamber from extremes of temperature and provide alternatives for finishes to give the chamber 10 an appearance that will allow it to be hung under the ceiling. The shell 11 has mounted on it a mounting spine 14. The spine 14 is of sufficient cross-section and strength to carry the chamber 10 and may be U-shaped to allow positioning and proper mounting of the shell 11. The spine 14, and thus shell 11 and germicidal cleansing chamber 10, are mounted to the ceiling by conventional mounting means such as suspension rods, cables or straps 13. Each of the mounting means 13 are attached to the mounting spine 14 by conventional means such as nut 70.

At either end of the elliptical central portion 16 of chamber 10 are end caps 23 and 24. The central portion 16 of the chamber 10 may be composed of a number of sections 100, 101, and 102 to allow access into the interior of the chamber 10. The central portion 16 and the end caps 23 and 24 may be made from spun aluminum or formed from a molded material having aluminum or other highly UV reflective material deposited on the interior.

Figure 2:
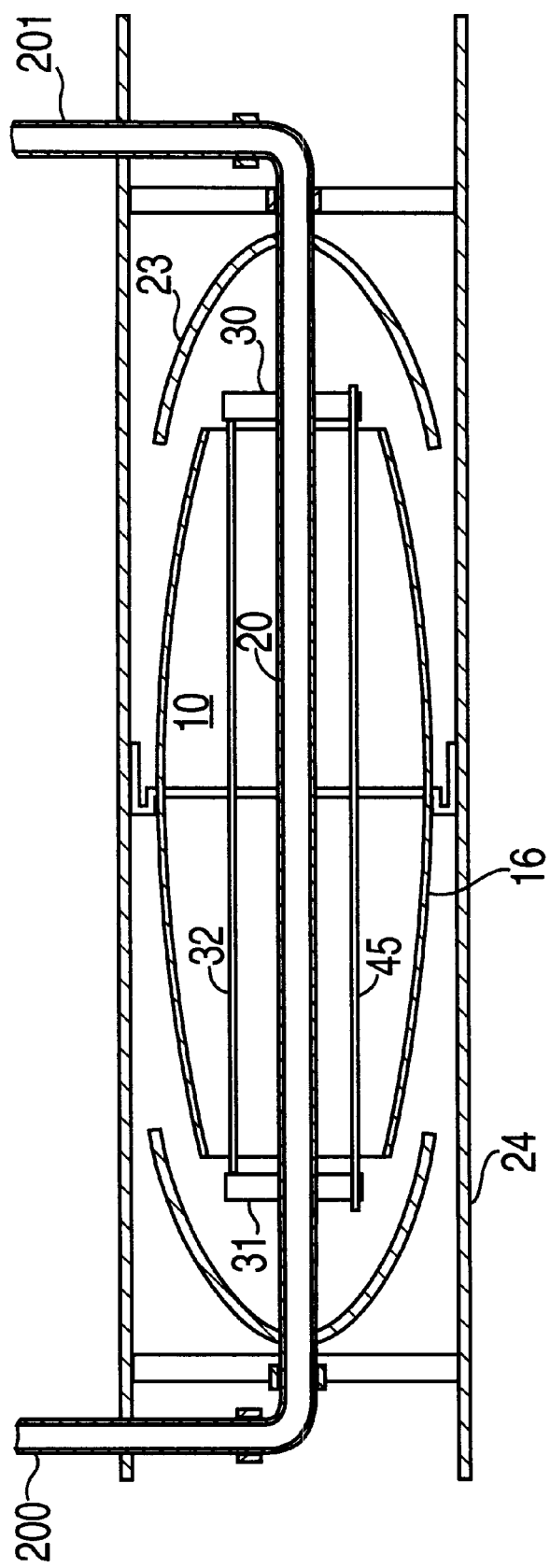
FIG. 2 is a cross-sectional view of the chamber FIG. 1.

The central portion 16 of the chamber 10 is an ellipsoid. The end caps 23 and 24 are displaced paraboloids which share a foci with the elliptical chamber. Normally, when mounted in a duct, it will be in the form of an elongated chamber as seen in FIGS. 1 and 2. However, the ellipsoid may be a sphere.

The bulkhead 25 is in sealed engagement with both the shell 11 and the central portion 16 of the chamber 10 at the mid-point of the central portion 16. As air is drawn into the duct system, it will be pass through the chamber 10, entering in the space between the end cap 23 and central portion 16. Since the chamber 10 can be mounted in existing duct systems, the air will be drawn into the chamber 10 by the circulation system of the duct system, such as a building HVAC fan.

Mounted in the chamber 10 are mounting rings 30 and 31 between which UV light sources 32 are positioned. Also attached to the mounting rings 30 and 31 are positioning rods 45 which hold the mounting rings 30 and 31 in their respective positions. For clarity of the drawings, only one UV light source 32 and one positioning rod 45 is shown. The number of UV light sources will be determined by the overall requirements of the system. The mounting rings 30 and 31 include an interior circuit board (not shown) protected by the structure of the mounting rings 30 and 31 from UV irradiation.

The chamber may be simply located in an existing duct system at a return vent or elsewhere. Adapters 50 and 51 on either side of shell 11 mate the chamber to a duct system preferably at or near a return air register.

Passing down the center of the chamber 10 is a UV transparent conduit 20. The conduit 20 is connected by conventional means to a conventional inlet pipe 200 and outlet pipe 201. Water or other fluids to be germicidally cleansed flow from the inlet pipe 200 through the chamber 10 and out the outlet pipe 201. The direction of flow can be reversed without effecting the cleansing efficiency. Pipes 200 and 201 pass through the duct walls 12 and are attached to the water distribution system. The water distribution system should be of such a design that only treated water can leave the pipes for use. The conduit 20 is shown positioned between the end caps 23 and 24. Alternatively, the UV transparent conduit 20 may enter and leave the chamber 10 through its central position 16 (not shown).

Because of the elliptical configuration of the body portion in conjunction with the effect of the parabolic end caps, the UV light generated by the UV light source is evenly dispersed throughout the extended length of the chamber 10. Any point in the chamber 10 receives the same quantity of UV light in all directions as any other point within the chamber 10. The formation of the walls of the chamber 10, by spinning and the qualities of aluminum from which it is spun, acts to ensure the greatest part of the energy generated by the UV light sources 32 is reflected back into the chamber 10 rather than being absorbed by the walls of the chamber. The effect of UV irradiation on a microorganism is dependent on both UV intensity and length of time of exposure to the UV irradiation. Since the walls are highly reflective, the irradiation intensity created reaches a steady state which is substantially greater than the output of the lamps and, because of the configuration, is evenly distributed through the chamber.

Figure 3:
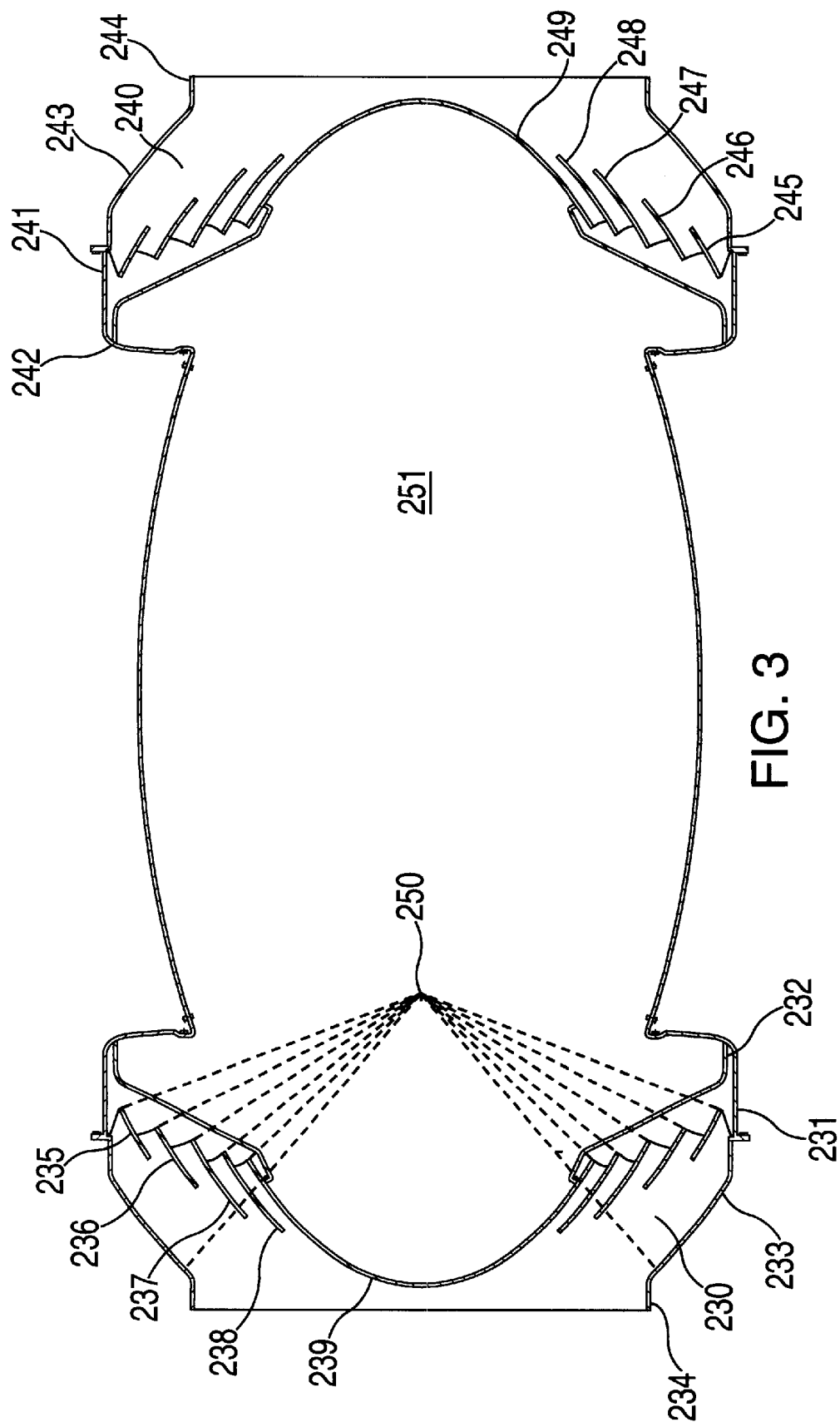
FIG. 3 is a cross-sectional view of another embodiment of the chamber of the present invention, not showing its ultraviolet light source or the ultraviolet transparent pipe, having a reflective grille at either end of the chamber.
Figure 4:
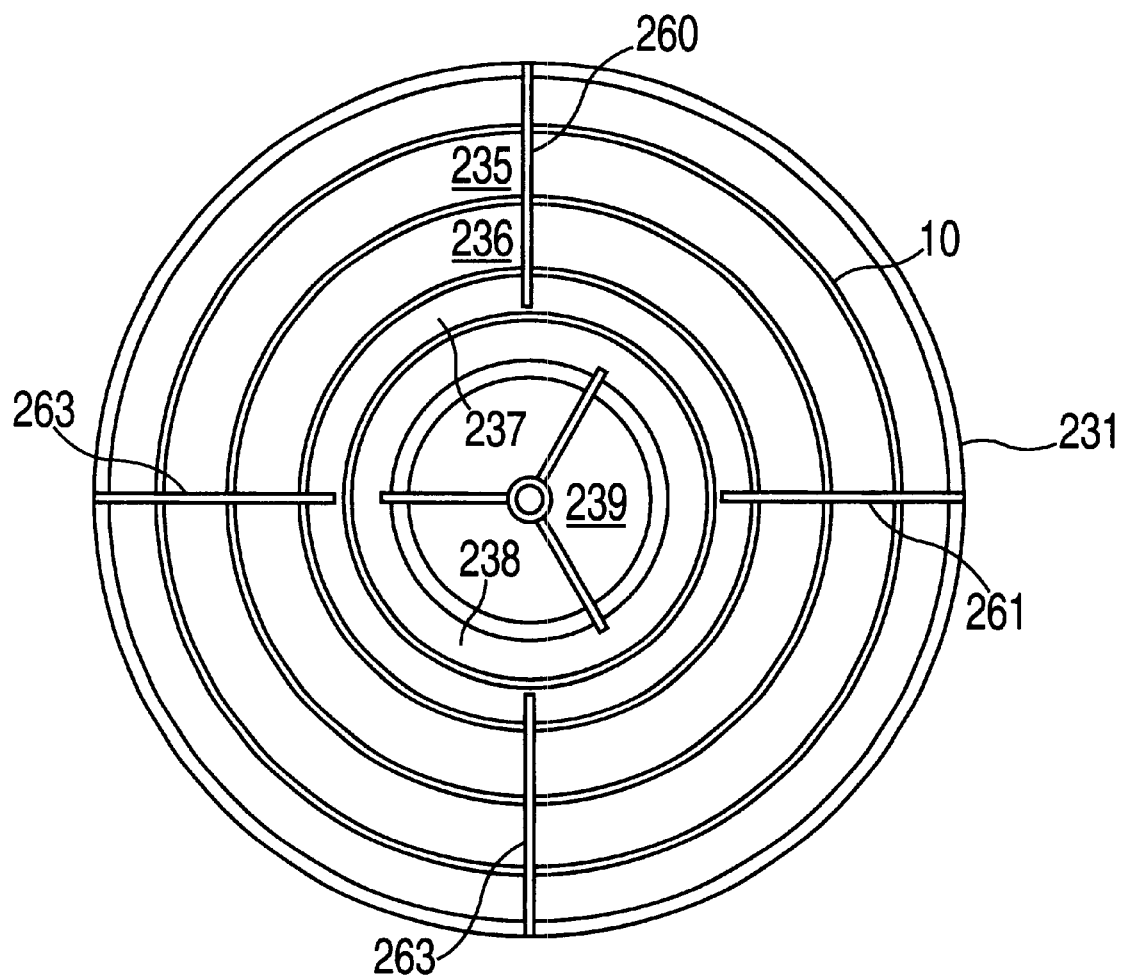
FIG. 4 is a sectional view at plane A—A of FIG. 3
Figure 5:
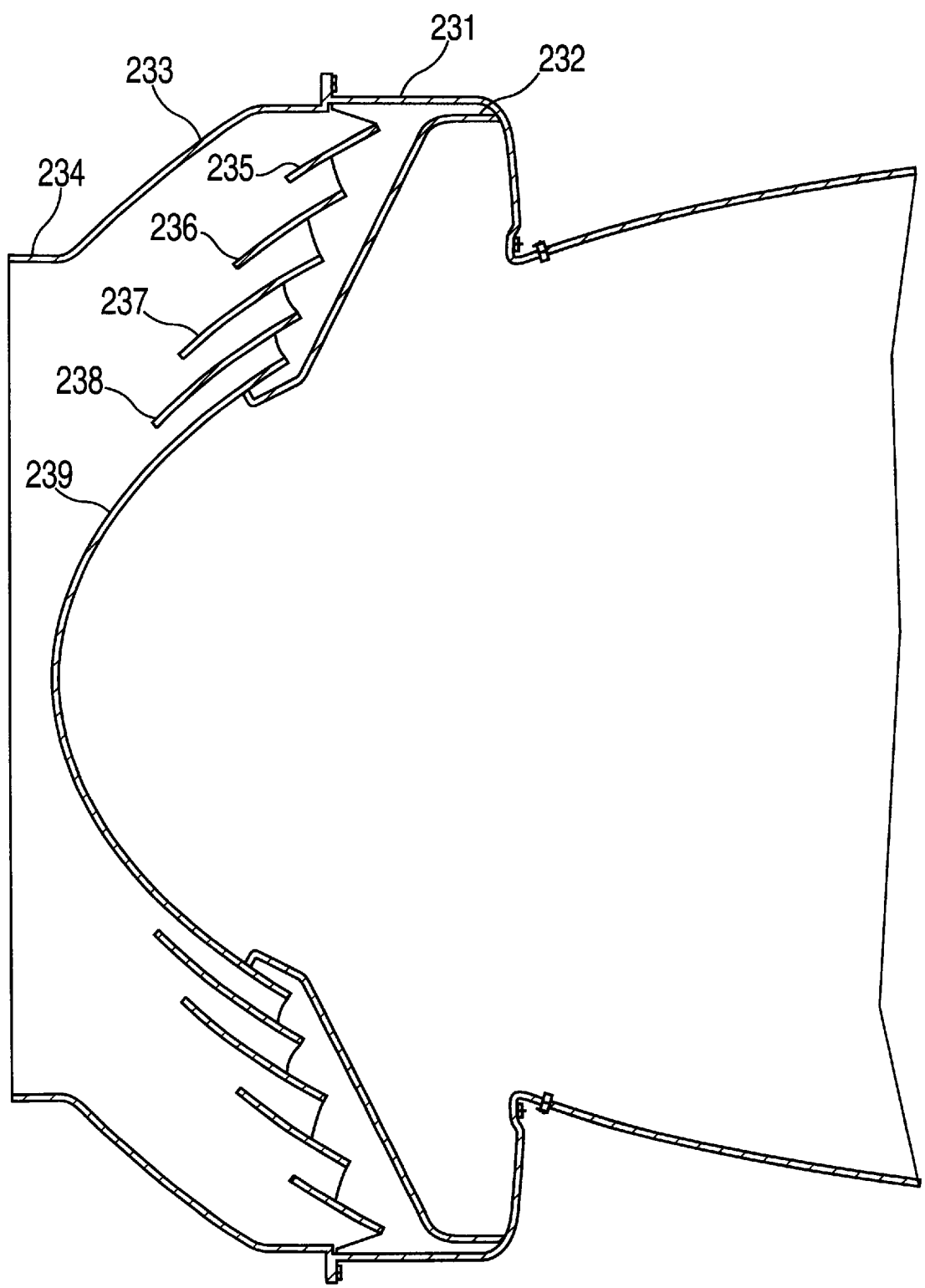
FIG. 5 is a partial enlarged view of one reflective grille of FIG. 3

In the embodiment of FIGS. 1 and 2, air passing through the duct system and into the chamber 10 must make a 180° turn around the end caps 23 and 24 to enter the chamber. This develops a back pressure which requires greater force to move air through the duct system. The present invention allows air to pass through the chamber 10 with the minimum diversion from a course along the chamber's major axis and less impediments to its free movement while, at the same time, not allowing UV energy to escape at the air inlet and outlet. In other words, the present system allows the passage of air almost unhindered in and out of the chamber 10, yet reflect substantially all the UV light back into the chamber 10 greatly reducing the energy requirements of the system. FIGS. 3, 4 and 5 disclose a chamber having a reflective grille structure of the present invention which accomplishes this end.

FIG. 3 is a cross-section of a germicidal air chamber with the new grille structure. Such grille configuration is equally useful in an air, water and combined air/water purification system where a central UV transparent conduit or pipe (not shown) may be positioned along the major axis of the chamber 10. End caps 23 and 24 are replaced with grilles 230 and 240 positioned in enlarged sections 231 and 241 of the chamber 10, all formed from UV reflective material.

The enlarged section 231 of the chamber 10 is formed from a cylindrical collar 232 and a truncated ellipsoidal section 233. The foci 250 of the truncated ellipsoidal section 233 is common with that of the chamber 10. The truncated ellipsoidal section 233 is joined with a second cylindrical collar 234 of reduced diameter which may mate with the duct 12 in which the unit is mounted or with an adapter (not shown) designed to mate it with the duct 12. Similarly, enlarged section 241 is formed from a cylindrical collar 242 and a truncated ellipsoidal section 243 having a cylindrical collar 244 for mating with the duct 12.

A grille is formed from a series of truncated sections of ellipsoids 235–239 and 245–249 having foci 250 and 251 common to the chamber 10 and with truncated ellipsoidal sections 233 and 243. As seen in FIG. 5, ellipsoidal grille elements 235–239 form a series of spatially separated steps having gaps in-between to allow the passage of air. The ellipsoidal grille elements 235–239 are held in place by fins 260–263. The center sections 239 and 249 forms a closed end of the chamber 10. The ellipsoidal grille elements 235–239 and 245–249, maintain reflective uniformity and common focal paths with the chamber 10, containing the light energy within the chamber 10. The spacing between the ellipsoidal grille elements 235–239 and 245–249, in combination with their surface length and positioning of the elements, is such that light energy coming directly from the ellipsoidal portion of chamber 10 hitting the surface of such grille 230 is reflected back into the chamber 10 as if there were only a single elliptical chamber.

The enlarged sections 231 and 241 are dimensioned so that the included angle of incident UV radiation is reflected back into the chamber 10 from any angle permitted by the chamber wall. The ellipsoidal grille elements 235–239 and 245–249 in combination with the inner surface of enlarged sections 231 and 241 act to reflect UV back into the chamber 10. Secondary reflections occurring between the ellipsoidal grille elements 235–239 and 245–249 tend to be reflected back into the chamber 10 by truncated ellipsoidal sections 233 and 243. Views into the chamber are equally blocked by the ellipsoidal grille elements 235–239 and 245–249.

The number of grille sections, their radial positioning and surface length are a function of the chamber 10 size and the desired air flow. The surface length of each ellipsoidal grille element 235–239 and 245–249 generally increases as their diameter and the radial spacing decreases.

FIG. 4 shows a view at plane A—A of FIG. 3. The ellipsoid grille elements 235–239 when viewed along the main axis of the ellipsoid chamber form a solid reflective wall and thus, act to reflect light back into the chamber nearly as efficiently as if there was a solid end cap while air is allowed to pass in the gap between the ellipsoid grille elements 235–239. In other words, the ellipsoid grille elements 235–239 and 245–249 form partially separated radial steps to provide air or fluid passage between them while containing UV radiation originating in the chamber 10. Ellipsoid grille elements 235–239 and 245–249 are held in place by struts 260, 261, 262 and 263.

The grille spacing is selected such that the cross-sectional area of the air passages between the ellipsoidal grille elements 235–239 and 245–249 is greater than that of the chamber 10 as truncated immediately before the enlarged sections 231 and 241, thereby compensating for the increased surface friction caused by the ellipsoidal grille elements 235–239 and 245–249, eliminating back pressure. In other words, the summation of the spacing between the ellipsoidal grille elements 235–239 and 245–249 is greater than the cross-section of the chamber as truncated immediately before the enlarged sections 231 and 241.

Figure 6:
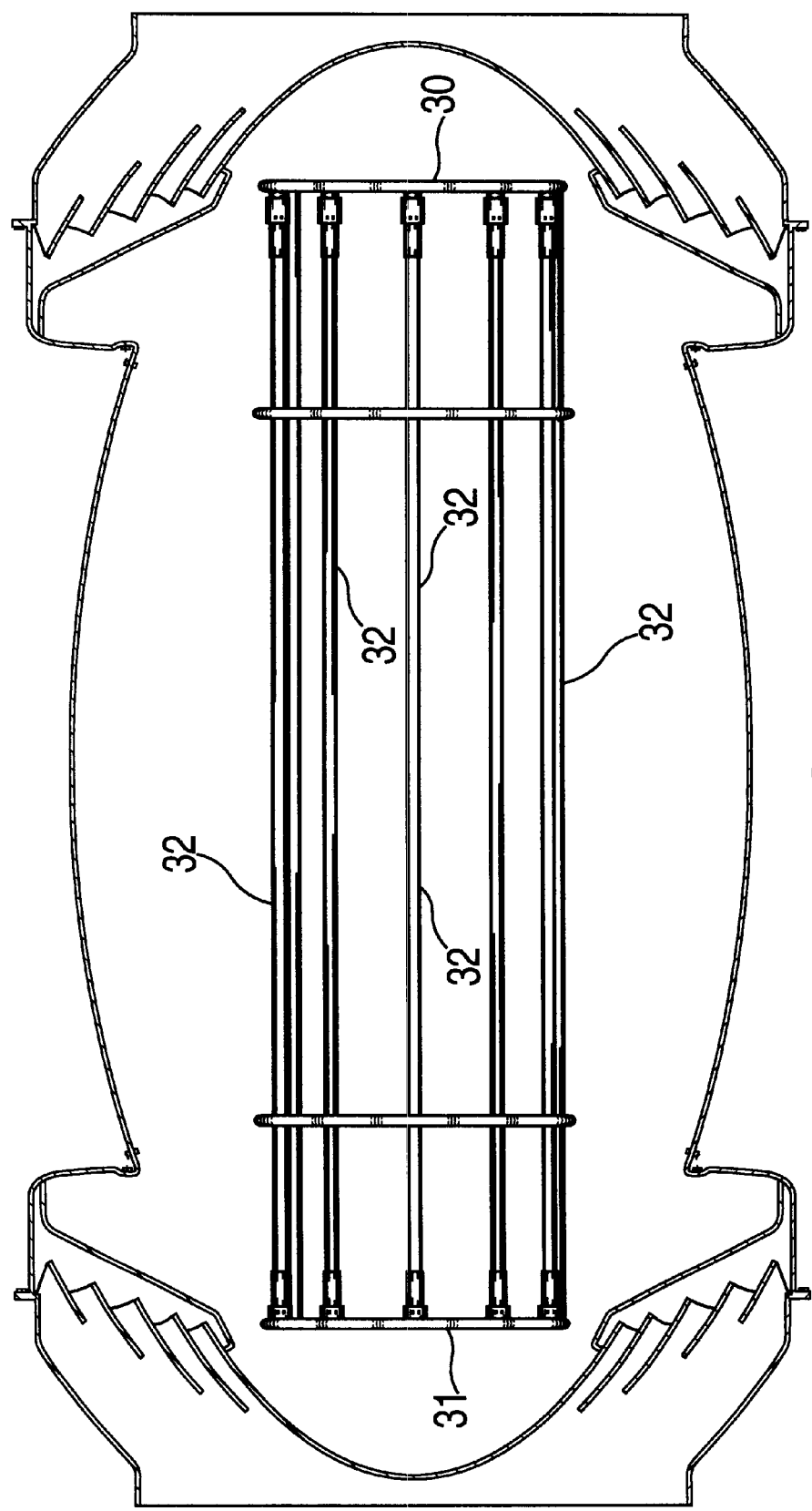
FIG. 6 is a cross-sectional view of the chamber of FIG. 3 having a multi-tube ultraviolet light source but not showing the ultraviolet transparent pipe.
Figure 7:
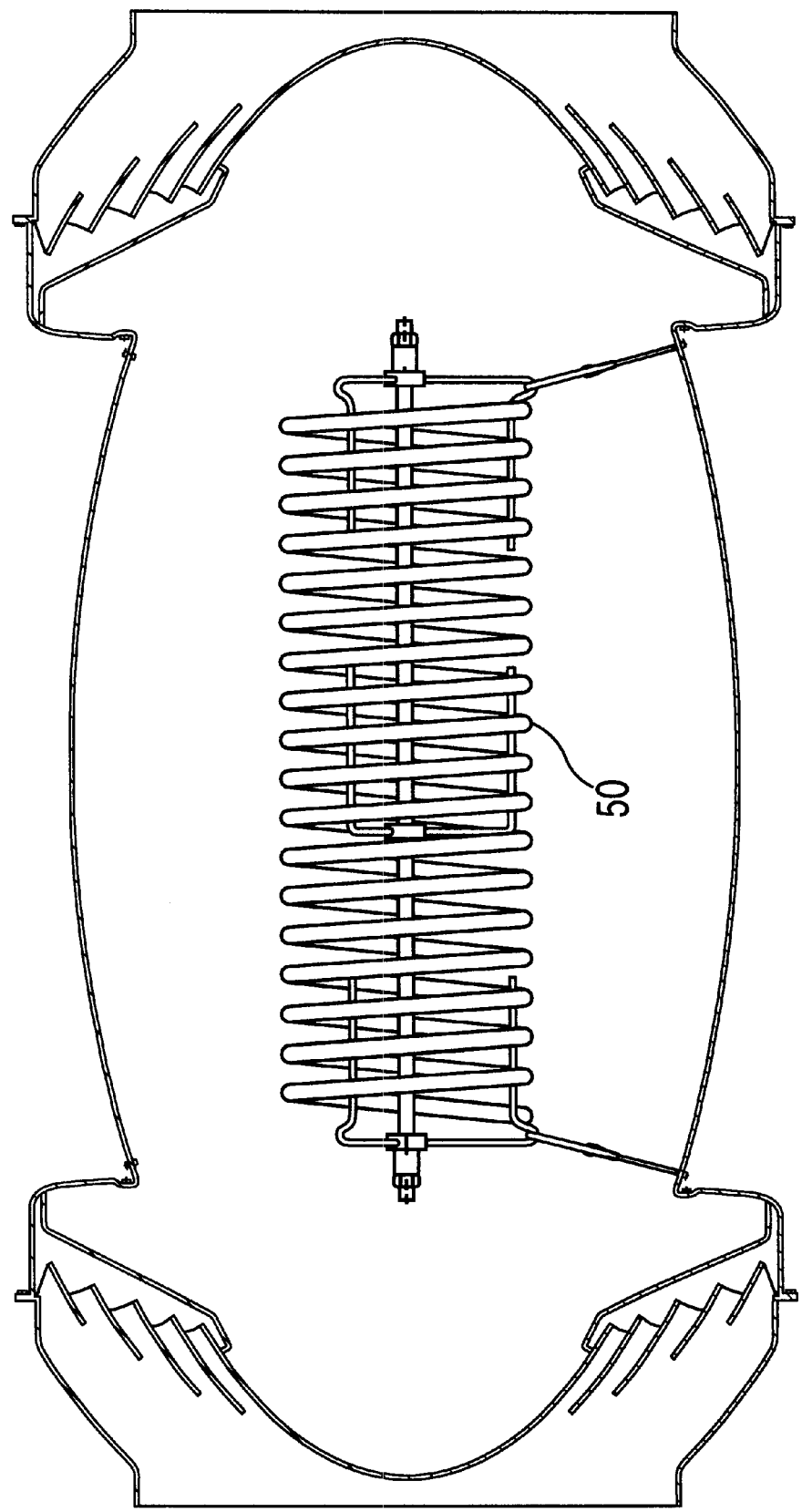
FIG. 7 is a cross-sectional view of the chamber of FIG. 3 having a helical tube ultraviolet light source but not showing the ultraviolet transparent pipe.

FIG. 6 discloses an array of linear UV tubes 32 between the ends 30 and 31. Due to the optic properties of the chamber 10, a UV light source positioned any place in the chamber 10 will result in a uniform distribution of energy throughout the chamber 10 and, thus, this lamp configuration, as any other lamp configuration, will result in a uniform distribution of light. However, the greater the distance traveled for any ray before its first reflection, incident with the wall, the more efficient the system since each reflection on the wall absorbs a certain amount of the UV energy. Thus, the most efficient system would have the light energy introduced at the geometric center of the ellipsoid chamber 10 as seen in FIG. 7.

To accomplish this, a helical UV source 50 with greater number of turns per inch at the center of the chamber 10 would result in a more efficient distribution of energy throughout the chamber 10 than the straight light tubes of FIG. 6. With the greater concentration of light toward the center of helical UV source 50, the greatest concentration of light energy would be generated in the center of the chamber 10 and, thus, the longer path before reflection would result in an undiminished use of the energy throughout the chamber. This helical formation is particularly useful in concentrating light on a UV transparent fluid conduit positioned along the major axis of the chamber 10.

Figure 8:
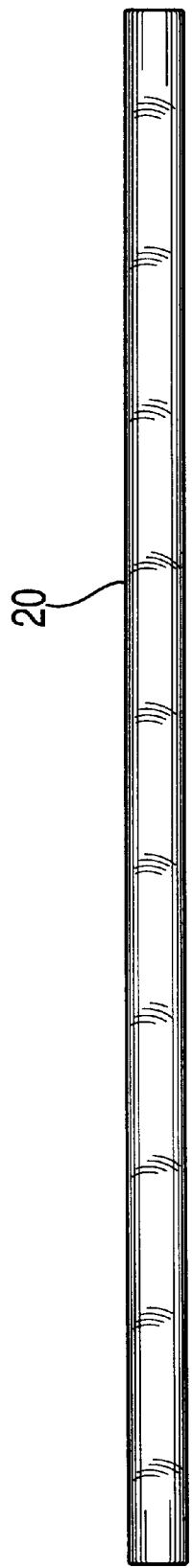
FIG. 8 is a cross-sectional view of a ultraviolet transparent pipe having straight sides.
Figure 9:
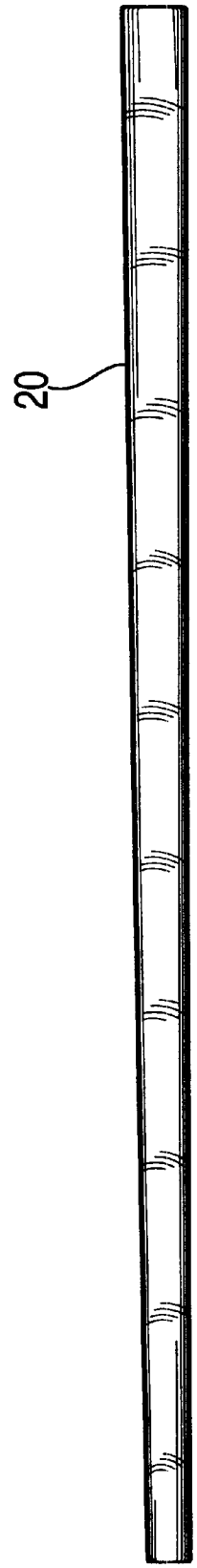
FIG. 9 is a cross-sectional view of a ultraviolet transparent pipe having tapered sides.
Figure 10:
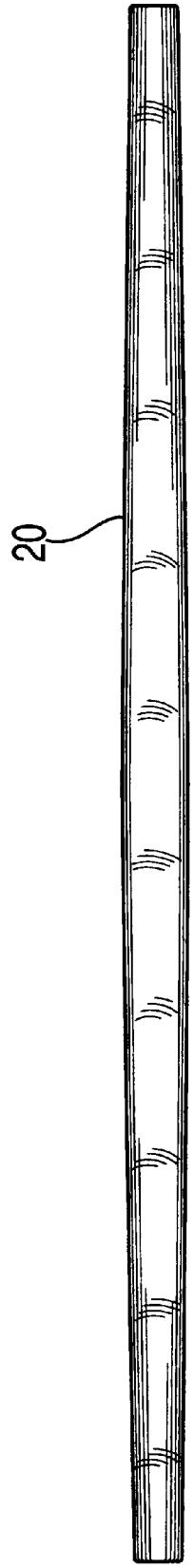
FIG. 10 is a cross-sectional view of a ultraviolet transparent pipe having symmetrically tapered sides.

As seen in FIGS. 8 through 10, a number of configurations of a UV transparent conduit are available. Of course, the conduit can be a simple conduit 20 of uniform dimension along its length as seen in FIG. 8. However, if the sides of the transparent conduit 20 are inclined to form a slender truncated cone, uniformly distributed light which enters the conduit would tend to be reflected back into the conduit rather than passing through the opposite wall of the conduit and into the chamber 10 as a whole. FIGS. 9 and 10 show two alternative arrangements to increase the reflectivity of the conduit 20. FIG. 9 shows a conduit 20 which is tapered over its entire length and FIG. 10 shows a conduit 20 which tapers from either end into an enlarged middle. Both configurations would tend to increase the concentration of UV light in the conduit 20 above that of the chamber 10 as a whole to increase germicidal cleansing of the denser fluid flowing through the conduit 20.

While the invention has been described as having a preferred design, it is understood that it is capable of further modification, uses and/or adaptations of the invention following in general principle of the invention and including such departures from the present disclosure as come within known or customary practice in the art to which the invention pertains, as may be applied to the central figures herein above set forth and fall within the scope of the invention of the limits of the appended claims.

I claim:

1. An apparatus for germicidally cleansing a gas comprising:
    a chamber positioned in a duct system having an inlet opening to allow the gas to enter the chamber and a separate exit opening to allow air to exit the chamber;
    the inlet and exit openings from the chamber include a grille formed from a series of spaced concentric elements;
    an ultraviolet light source positioned in the chamber;
    the internal walls of the chamber and grille being made from an ultraviolet reflective material and the walls of the chamber shaped to direct ultraviolet light into and upon the walls of the chamber uniformly throughout the chamber and such that the energy in the chamber accumulates over time to reach a uniform steady state energy level greater than that emitted by the UV source; and
    an adapter to mate the chamber with the duct system.

2. An apparatus according to claim 1, wherein a substantial portion of the chamber is in the shape of a truncated ellipsoid.

3. An apparatus according to claim 2, wherein the concentric grille elements are in the form of truncated ellipsoids.

4. An apparatus according to claim 3, wherein the concentric grille elements are housed in an section of the chamber which is larger in cross-section than the truncated ellipsoidal section of chamber at the intersection of the enlarged section and the truncated ellipsoidal section of chamber.

5. An apparatus according to claim 4, wherein the grille is larger in cross-section than the truncated ellipsoid of the chamber at the intersection of the enlarged portion and the truncated section of the chamber.

6. An apparatus according to claim 3, wherein one wall of the enlarged section of the chamber is a truncated ellipsoid.

7. An apparatus according to claim 4, wherein the truncated ellipsoid portion of the chamber and the truncated ellipsoidal grille elements have a common foci.

8. An apparatus according to claim 6, wherein the truncated ellipsoid portion of the chamber, the truncated ellipsoidal grille elements and the truncated ellipsoidal wall of the enlarged section of the chamber have a common foci.

9. An apparatus according to claim 8, wherein the spacing between the ellipsoidal grille elements, their surface length, the truncated ellipsoidal wall of the enlarged section of the chamber, and their positioning are such that UV light from the unsealed ellipsoidal portion of the chamber hitting the surface of the grille is reflected back into the chamber.

10. An apparatus according to claim 8, wherein the spacing between the ellipsoidal grille elements, their surface length, the truncated ellipsoidal wall of the enlarged section of the chamber, and their positioning are such that all of the UV rays emitted from the UV light source are incident upon ellipsoidal surfaces of common foci upon their first reflection within the chamber.

11. An apparatus according to claim 8, wherein the spacing between the ellipsoidal grille elements, their surface length, the truncated ellipsoidal wall of the enlarged section of the chamber, and their positioning at the inlet and exit openings provide low pressure resistance to the gasses flowing through the chamber.

12. An apparatus according to claim 8, where the spacing between the ellipsoidal grille elements, their surface length, the truncated ellipsoidal wall of the enlarged section of the chamber, and their positioning are symmetrical.

13. An apparatus according to claim 8, wherein the spacing between the ellipsoidal grille elements, their surface length, the truncated ellipsoidal wall of the enlarged section of the chamber, and their positioning permit the gasses to flow in and out of the chamber under low pressure while containing reflective energy of a light source located within.

14. An apparatus according to claim 2, wherein a UV transparent conduit runs through at least a part of the chamber to allow germicidal treatment of a fluid passing through the conduit.

15. An apparatus according to claim 14, wherein the walls of the conduit are shaped to retain UV radiation in the conduit.

16. An apparatus according to claim 14, wherein the UV transparent conduit is in the form of a least one truncated cone.

17. An apparatus according to claim 14, wherein the UV transparent conduit is in the form of two truncated cones where the base of the truncated cones are connected together.

18. An apparatus for germicidally cleansing a fluid comprising:
    a chamber;

an ultraviolet light source positioned in the chamber;

the internal walls of the chamber being made from an ultraviolet reflective material and the walls of the chamber shaped to direct ultraviolet light into and upon the walls of the chamber uniformly throughout the chamber and such that the energy in the chamber accumulates over time to reach a uniform steady state energy level greater than that emitted by the UV source;

a UV transparent conduit which runs through the chamber; and, walls of the UV transparent conduit are shaped to retain UV radiation in the conduit.

19. An apparatus according to claim 18, wherein the UV transparent conduit is in the form of a least one truncated cone.

20. An apparatus according to claim 18, wherein the UV transparent conduit is in the form of two truncated cones where the base of the truncated cones are connected together.

\* \* \* \* \*